(12) United States Patent
Huebner et al.

(10) Patent No.: US 8,231,627 B2
(45) Date of Patent: Jul. 31, 2012

(54) INSERTION TOOL FOR BONE PLATES

(75) Inventors: Randall J. Huebner, Portland, OR (US); Joel Gillard, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 825 days.

(21) Appl. No.: 12/176,913

(22) Filed: Jul. 21, 2008

(65) Prior Publication Data

US 2009/0076554 A1     Mar. 19, 2009

Related U.S. Application Data (60) Provisional application No. 60/961,317, filed on Jul. 19, 2007.

(51) Int. Cl.
*A61B 17/68* (2006.01)

(52) U.S. Cl. .......... 606/86 B; 606/99; 606/280

(58) Field of Classification Search ........... 606/86 B, 606/99
See application file for complete search history.

(56) References Cited

U.S. PATENT DOCUMENTS

| | | | |
|---|---|---|---|
| 4,923,471 A * | 5/1990 | Morgan ........................ | 606/60 |
| 4,959,065 A | 9/1990 | Arnett et al. | |
| 5,487,741 A | 1/1996 | Maruyama et al. | |
| 5,667,480 A * | 9/1997 | Knight et al. ................. | 600/210 |
| 5,947,970 A | 9/1999 | Schmelzeisen et al. | |
| 5,957,927 A | 9/1999 | Magee et al. | |
| 6,916,323 B2 | 7/2005 | Kitchens | |
| 7,153,309 B2 | 12/2006 | Huebner et al. | |
| 7,635,366 B2 * | 12/2009 | Abdou ........................... | 606/71 |
| 2003/0004513 A1 * | 1/2003 | Guzman et al. ................. | 606/62 |
| 2004/0147812 A1 | 7/2004 | Hamel | |
| 2005/0010226 A1 | 1/2005 | Grady, Jr. et al. | |
| 2006/0004361 A1 | 1/2006 | Hayeck et al. | |
| 2006/0116679 A1 | 6/2006 | Lutz et al. | |
| 2006/0155298 A1 | 7/2006 | Mueller et al. | |
| 2006/0173465 A1 * | 8/2006 | Meridew et al. ................ | 606/99 |
| 2009/0069851 A1 | 3/2009 | Gillard et al. | |

OTHER PUBLICATIONS

Synthes® (USA), Less Invasive Stabilization System (LISS), Technique Guide, Distal Femur; combination surgery instructional technique guide and product brochure (2000).

* cited by examiner

*Primary Examiner* — Nicholas Woodall
(74) *Attorney, Agent, or Firm* — Kolisch Hartwell, PC (57) ABSTRACT

System, including methods, apparatus, kits, and components, for installation of a bone plate using an insertion tool attached to a bone plate and providing a blade for lifting soft tissue off bone in front of the bone plate as the insertion tool is advanced along a surface of the bone.

20 Claims, 5 Drawing Sheets

INSERTION TOOL FOR BONE PLATES

CROSS-REFERENCE TO PRIORITY APPLICATION

This application is based upon and claims the benefit under 35 U.S.C. §119(e) of U.S. Provisional Patent Application Ser. No. 60/961,317, filed Jul. 19, 2007, which is incorporated herein by reference in its entirety for all purposes.

BACKGROUND

The human skeleton is composed of 206 individual bones that perform a variety of important functions, including support, movement, protection, storage of minerals, and formation of blood cells. These bones can be grouped into two categories, the axial skeleton and the appendicular skeleton. The axial skeleton consists of 80 bones that make up the body's center of gravity, and the appendicular skeleton consists of 126 bones that make up the body's appendages. The axial skeleton includes the skull, vertebral column, ribs, and sternum, among others, and the appendicular skeleton includes the long bones of the upper and lower limbs, and the clavicles and other bones that attach these long bones to the axial skeleton, among others.

To ensure that the skeleton retains its ability to perform its important functions, and to reduce pain and disfigurement, fractured bones should be repaired promptly and properly. Typically, fractured bones are treated using fixation devices that reinforce the fractured bones and keep them aligned during healing. Fixation devices may take a variety of forms, including casts and external fixators for external fixation, and bone plates, wires, and/or threaded fasteners (e.g., bone screws) for internal fixation.

Bone plates are implants that may be positioned under skin and other soft tissue for mounting on the bone adjacent the fracture. These plates may be manufactured and/or custom bent for mounting to particular regions of bone. To use a bone plate to repair a fractured bone, a surgeon (1) selects an appropriate plate, (2) reduces (sets) the fracture, and (3) fastens the plate to the bone on opposing sides of the fracture using suitable fasteners, such as bone screws, so that the bone plate spans the fracture and fragments of the bone are substantially fixed in position.

A potential disadvantage to the use of bone plates is the amount of tissue damage produced by installation. For example, to access a target site on bone, a bone plate may be placed onto the bone through an incision in soft tissue that overlaps much of the target site and is comparable in size to the length of the bone plate. Alternatively, to reduce the amount of injury to soft tissue, the bone plate may be inserted through an incision that is shorter than the bone plate. In this case, the bone plate only partially overlaps the incision and extends away from the incision under soft tissue. However, the bone plate may be difficult to advance under soft tissue to achieve this partial overlap with the incision.

To facilitate advancement under soft tissue, bone plates may be manufactured with a beveled end. However, for practical reasons, the beveled end generally is too rigid and blunt to be effective. First, the flexibility of the beveled end may be limited by the composition of the bone plate, which is typically metal. Second, if the beveled end were to be fabricated as very thin, such a thin beveled end would create a segment of the bone plate that is not rigid enough to be effective for bone fixation, thereby reducing the effective length of the bone plate. Third, if the beveled end were to be fabricated as relatively sharp to facilitate separation of soft tissue and bone, the sharp beveled end may produce tissue irritation over time as tissue rubs against the end of the bone plate after its installation. Accordingly, other approaches to installing bone plates under soft tissue are needed.

SUMMARY

The present disclosure provides a system, including methods, apparatus, kits, and components, for installation of a bone plate using an insertion tool attached to a bone plate and providing a blade for lifting soft tissue off bone in front of the bone plate as the insertion tool is advanced along a surface of the bone.

DETAILED DESCRIPTION

The present disclosure provides a system, including methods, apparatus, kits, and components, for installation of a bone plate using an insertion tool attached to a bone plate and providing a blade for lifting soft tissue off bone in front of the bone plate as the insertion tool is advanced along a surface of the bone.

The apparatus may include an assembly of a bone plate attached to an insertion tool. For example, the bone plate may be engaged with the insertion tool in a friction fit or locked to the insertion tool (such as via a threaded fastener disposed in threaded engagement with the bone plate or via a slidable detent, among others). The insertion tool may include an internal portion connected to an external portion. The internal portion may form an inner arm and the external portion may form an outer arm. The inner and outer arms may extend at least substantially parallel to one another from a bridge region of the insertion tool to form a generally U-shaped body. The internal portion (and/or inner arm) may engage the bone plate and may be configured to be placed generally between soft tissue and bone of a patient. The internal portion (and/or inner arm) may include opposing trailing and leading ends that define a direction of advancement of the bone plate. The leading end may be forward of the bone plate with respect to the direction of advancement. The trailing end may or may not extend rearward of the bone plate. The external portion (and/or outer arm) may be connected to the internal portion (and/or inner arm) through the trailing end of the internal portion (and/or inner arm). The external portion (and/or outer arm) may provide a handle to permit aiming and/or positioning of the internal portion (and/or inner arm) from outside the patient. In addition, the external portion (and/or outer arm) may include a targeting guide defining openings that are coaxial with apertures of the bone plate.

The insertion tool may provide a spatula implement including a blade formed by the internal portion, the inner arm, and/or the leading end forward of the bone plate. At least part of the blade may taper in thickness away from the bone plate, that is, generally in the direction of advancement defined by the internal portion. The blade and the bone plate may be generally coplanar. The blade may be configured to lift soft tissue from the bone ahead of the bone plate as the internal portion (and/or inner arm) is advanced (i.e., moved in a forward direction) in the direction of advancement. Accordingly, the blade may have a geometry and composition to promote lifting soft tissue from bone. For example, the blade may be flexible (i.e., more flexible than the bone plate), which may allow the blade to flex laterally and/or longitudinally as it travels between soft tissue and bone, to conform the shape of the blade to the bone surface. To provide this flexibility, the blade may be thinner than the bone plate (i.e., the blade may have an average thickness that is less than the average thickness of the bone plate) and/or may be formed of a more flexible material than the bone plate (e.g., a plastic blade and a metal bone plate). Alternatively, or in addition, the blade may taper longitudinally and/or laterally. For example, to form a longitudinal taper, the blade may have opposing inner and outer surfaces, with the outer surface being at least partially sloped toward the inner surface in a direction away from the bone plate generally along the direction of advancement. Alternatively, or in addition, to form a bilateral taper, the outer surface of the blade may include a pair of laterally disposed regions that slope in respective opposing directions generally orthogonal to the direction of advancement. Furthermore, the blade may have an edge that is sharper than an adjacent end (i.e., the leading end) of the bone plate and/or that is sharp enough to travel readily between bone and soft tissue as the blade is advanced in direction of advancement. However, the edge of the blade may be blunt enough to restrict cutting soft tissue. The edge may be linear or curved, among others.

The present disclosure also provides a method of installing a bone plate. An insertion tool attached to a bone plate may be selected. The insertion tool may provide a blade formed forward of the bone plate and tapering in thickness generally in a direction of advancement defined by the insertion tool. The insertion tool may be moved in the direction of advancement along a surface of bone such that soft tissue is lifted off the surface of bone by the blade ahead of the bone plate.

The installation system disclosed herein may solve a number of problems presented by use of a bone plate to lift soft tissue off bone. In particular, by forming a blade on an insertion tool, the blade may have characteristics (i.e., flexibility, composition, size, shape, sharpness, etc.) that are undesirable and/or impractical to introduce into the leading end of a bone plate. Therefore, installation of a bone plate using the insertion tool may be less damaging to soft tissue and may provide improved manipulation and positioning of a bone plate.

The following sections describe further aspects of the present disclosure, including, among others, (I) exemplary installation apparatus, (II) exemplary methods of installing a bone plate, (III) composition of system components, (IV) kits for installing bone plates, and (V) examples.

I. Exemplary Installation Apparatus

Figure 1:
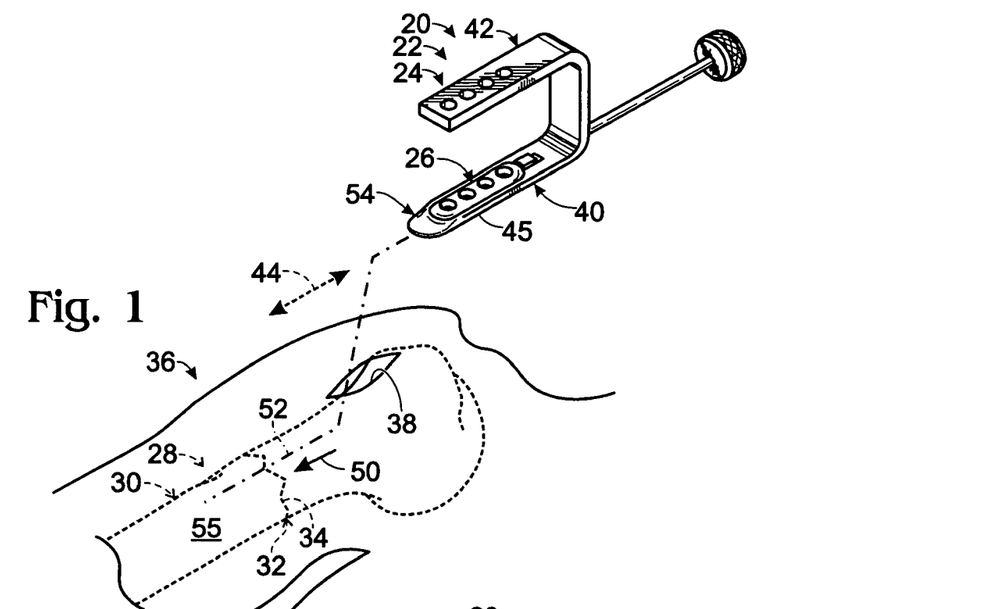
FIG. 1 is a view of selected components of an exemplary installation system, particularly an installation apparatus of the system that employs an insertion tool attached to a bone plate, with an advancement path of the installation apparatus indicated with respect to a fractured humeral bone, in accordance with aspects of the present disclosure.
Figure 2:
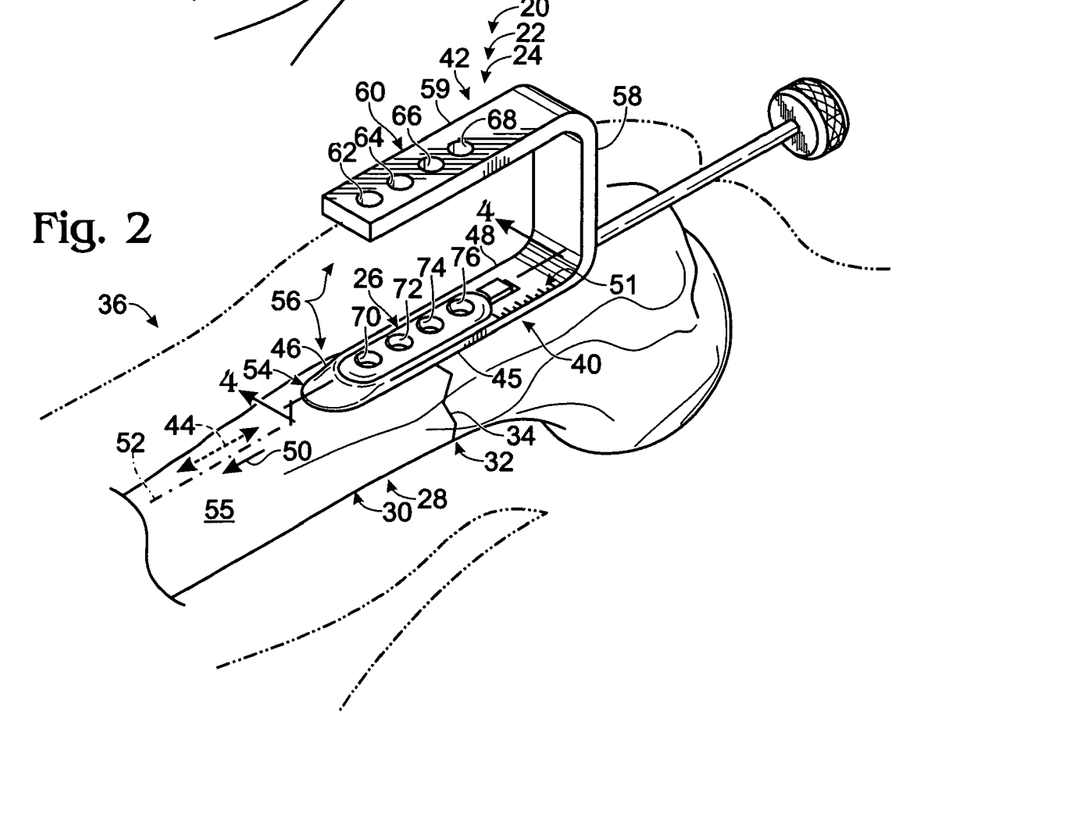
FIG. 2 is a view of the installation apparatus of FIG. 1 during or after advancement of the installation apparatus under soft tissue along the humeral bone.

FIGS. 1 and 2 show views of selected components of an exemplary installation system 20 employing an installation apparatus 22 that utilizes an insertion tool 24 attached to a bone plate 26. The installation apparatus may be used to position the bone plate under soft tissue on a bone 28 (such as a humeral bone 30) that has a discontinuity 32, such as a fracture 34. FIGS. 1 and 2 show installation apparatus 22 respectively before and after the apparatus is placed on humeral bone 30 of a patient 36 through an incision 38 in soft tissue and along the humeral bone. Installation apparatus 22 may be described as providing or including (1) a holder for a bone plate, (2) a spatula implement that lifts soft tissue off bone ahead of the bone plate, and/or (3) a targeting guide for guiding formation of incisions in soft tissue and/or holes in bone, and/or movement of fasteners through apertures of a bone plate, among others. To provide these structures, insertion tool 24 may include an internal portion 40 connected to an external portion 42.

Internal portion 40 may be configured to be disposed temporarily inside the body of patient 36 during bone plate installation and to be placed generally between soft tissue and bone of the patient. The internal portion thus may have a low profile and may be sized and shaped to minimize undesired damage to surrounding soft tissue as it is moved through incision 38 and between bone and soft tissue. For example, the internal portion may have smooth contours and rounded edges. Internal portion 40 (and/or the bone plate) may be elongate to define a long axis 44.

Bone plate 26 may be attached to the insertion tool by engagement with internal portion 40. When the bone plate and the insertion tool are attached, internal portion 40 and bone plate 26 may have long axes that are at least substantially parallel or collinear to one another.

Bone plate 26 and internal portion 40 may have any suitable relative thickness and width dimensions. For example, the internal portion may have a thickness (and/or width) that is less than about twice or no more than about 50% greater than the thickness (and/or width) of the bone plate. Alternatively, the internal portion may have a thickness (and/or width) that is about the same as or less than the thickness (and/or width) of the bone plate.

Internal portion 40 may form an inner arm 45 that includes opposing leading and trailing ends 46, 48 (see FIG. 2), which define a direction of advancement 50. The leading and trailing ends may or may not extend respectively forward and rearward of the bone plate along long axis 44. The terms "forward" and "rearward," as used herein, are with respect to direction of advancement 50, with "forward" being in the direction of advancement and "rearward" being opposite the direction of advancement (i.e., in the direction of retraction). Based on whether or not the trailing end extends rearward of the bone plate, the internal portion may have a length that is greater than, about the same as, or less than the length of the bone plate, but the internal portion typically is longer than the bone plate. In some embodiments, trailing end 48 may have a length, measured rearward of the bone plate, that is at least about as great as or greater than the distance that the trailing boundary of the bone plate is advanced under soft tissue (e.g., from incision 38) during bone plate installation.

Reference marks 51 (also termed graduations) may be disposed along the long axis of the internal portion, particularly along trailing end 48. The reference marks may be configured to permit measurement of an insertion distance of the insertion tool and/or the bone plate under soft tissue. For example, the reference marks may be spaced uniformly to form a metric or English-unit scale. The reference marks may be formed on an outer surface of the trailing end, such as by etching, embossing, addition of a surface layer, or the like. One or more individual reference marks optionally may be identified by an alphanumeric symbol, particularly a number.

Leading end 46 may travel ahead of (in front of) the bone plate to create a path 52 for the bone plate. Leading end 46 may form a blade 54 that effects or promotes separation of soft tissue from bone 28 as the internal portion is advanced (in direction 50) along a surface 55 of the bone. The insertion tool thus may be described as providing a spatula implement 56 (also termed an elevator implement), which includes blade 54 connected to a handle formed by external portion 42.

External portion 42 may be configured to be disposed outside of patient 36 during installation of the bone plate. The external portion thus may include a bridge region 58 that extends generally from trailing end 48 of internal portion 40 to an elongate aiming structure or outer arm 59 (see FIG. 2). Bridge region 58 may connect internal portion 40 (and/or inner arm 45) to outer arm 59 and may at least partially define the relative positions of the inner and outer arms. Outer arm 59 (and/or bridge region 58) may function as a handle, such that the insertion tool can be grasped and manipulated by hand. Accordingly, the external portion permits positioning of the internal portion and its engaged bone plate from outside the patient when the internal portion is placed between soft tissue and bone. Outer arm 59 may be at least substantially parallel to and may extend in substantially the same direction as inner arm from bridge region 58, to allow the bone plate to be aimed based on the orientation of the outer arm. Accordingly, the inner and outer arms may extend at least substantially parallel to one another from bridge region 58 to form a generally U-shaped body.

The external portion (e.g., outer arm 59) also may include a targeting guide 60 (also termed a guide region) for guiding a scalpel, a hole forming tool (i.e., a drill), a fastener, and/or a tip of a driver, among others. The targeting guide may define one or more guide paths that extend through one or more apertures of the bone plate. For example, the targeting guide may define one or more openings 62-68 that are aligned with (i.e., coaxial with) respective apertures 70-76 of bone plate 26. (The terms "opening" and "aperture," as used in the present disclosure, are intended to have the same meaning.)

Figure 3:
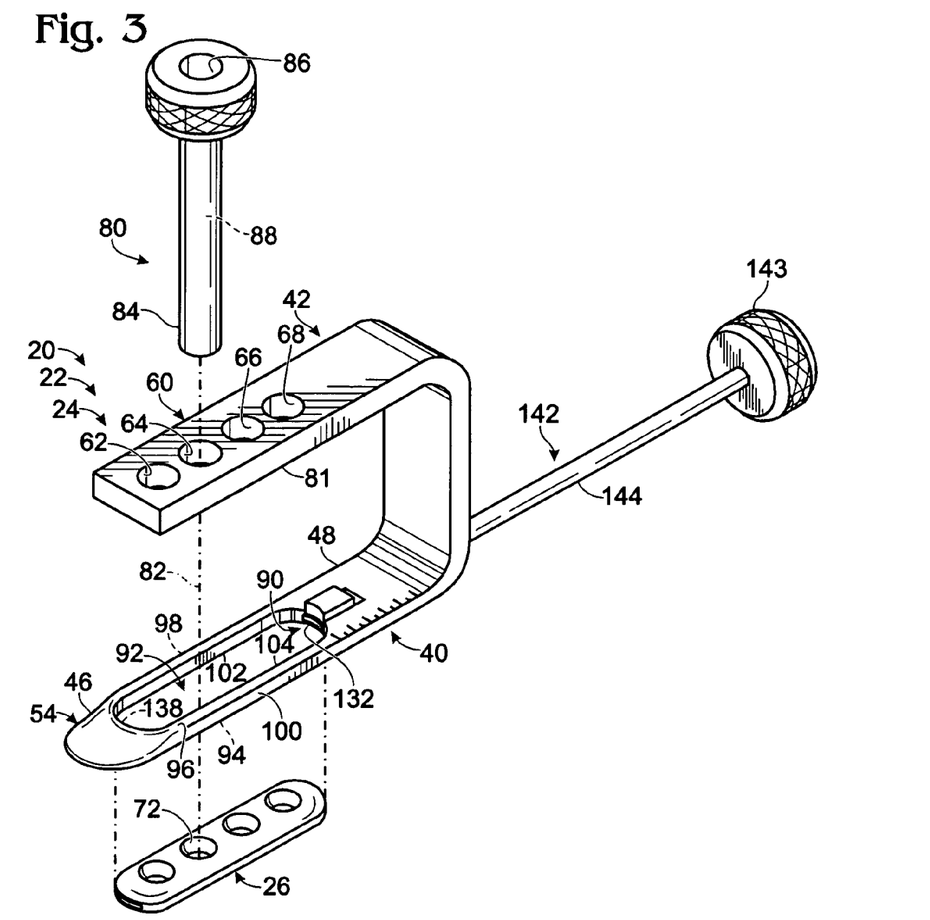
FIG. 3 is an exploded view of the installation system of FIG. 1 in the absence of the humeral bone, with the system also including a guide element that may be connected to the insertion tool to guide hole formation and/or fastener placement, in accordance with aspects of the present disclosure.

FIG. 3 shows an exploded view of installation system 20 in the absence of the humeral bone. Insertion tool 24 may include at least one guide element 80 that is coupled or couplable to a body of targeting guide 60 (e.g., coupled to outer arm 59). The guide element may be structured to be received in one or more of openings 62-68, and in turn may receive and guide translational movement of a knife, a hole-forming tool (a drill), a fastener, and/or a driver along a guide path to an aperture(s) of the bone plate. For example, here, guide element 80 defines a guide path 82 extending through aperture 72 of bone plate 26. The guide element may be attached removably to the body of the targeting guide (e.g., outer arm 59), or may be formed integrally with the body. If attached removably, the guide element may be slidable into and out of each opening 62-68 of the targeting guide body. For example, guide element 80 may be removed from opening 64 and placed into another opening (62, 66, or 68) to define another guide path extending through a corresponding aperture of the bone plate. In some embodiments, insertion tool 24 may be provided with a distinct guide element for each opening 62-68.

The guide element may have any suitable structure. For example, the guide element may include a hollow cylinder or a tube 84 (which may be or include a cannula) that defines an elongate passage or opening 86 for receiving a knife, a drill bit, a fastener, and/or a driver tip, among others. The guide element may include indicia 88 arranged along the guide element, and visible on the guide element, to facilitate measuring the translational position of the guide element with respect to body 81 (and/or internal portion 40).

Insertion tool 24 may be structured to receive a bone plate. In particular, internal portion 40 may include a coupling mechanism 90 for engagement of the bone plate. Coupling mechanism 90 may hold the bone plate in a substantially fixed configuration with respect to the internal portion (and/or insertion tool). The coupling mechanism may, for example, include a cavity 92 defined by internal portion 40 for receiving bone plate 26. Leading end 46 and trailing end 48 of internal portion 40 may opposingly flank cavity 92.

The cavity may have any suitable shape. For example, the cavity may be shaped for receiving the bone plate from below (and toward) an inner surface (bone facing surface) 94, from above (and toward) an outer surface (bone opposing surface) 96, and/or from one or both sides/edges 98, 100 of internal portion 40. Here, cavity 92 is shaped to receive bone plate 26 from inner surface 94, that is, from below internal portion 40 if tool 24 is oriented as shown in FIG. 3. The cavity may be shaped in correspondence with the bone plate. For example, the cavity may have a perimeter wall shaped in correspondence with at least a portion of the perimeter of the bone plate.

Alternatively, or in addition, the cavity may include one or more through-holes that are co-axial with one or more apertures of the bone plate. The cavity also or alternatively may include one or more recesses formed in inner surface 94 of internal portion 40 and configured to receive at least a portion of the bone plate. In any event, cavity 92 may receive any suitable portion of bone plate 26, such that internal portion 40 (and/or inner arm 45) covers any suitable portion of the outer surface of the bone plate, including none of the outer surface, only a perimeter region of the outer surface, most of the outer surface (e.g., not extending over the apertures of the bone plate), or the like. In some embodiments, internal portion 40 may include a pair of spanning members 102, 104 that opposingly flank cavity 92 laterally and that extend generally longitudinally along internal portion 40, from leading end 46 to trailing end 48 of the internal portion.

Figure 4:
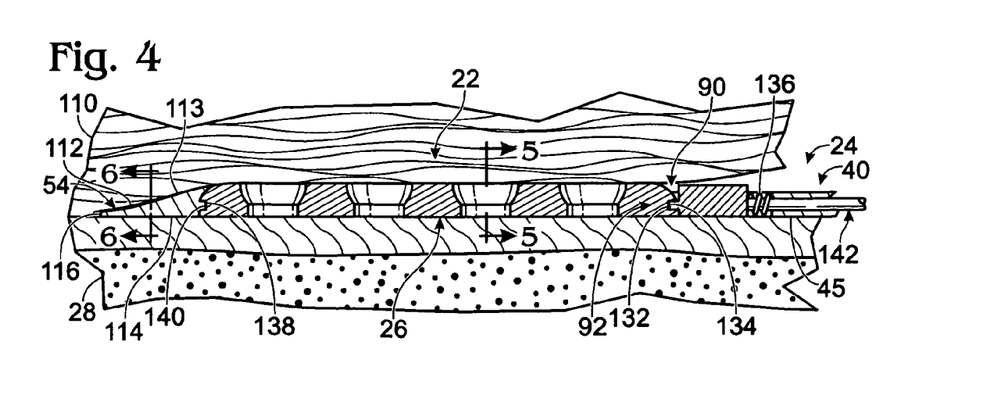
FIG. 4 is a longitudinal sectional view of the humeral bone, overlying soft tissue, and insertion apparatus of FIG. 2, taken generally along line 4-4 of FIG. 2.

FIG. 4 shows a longitudinal sectional view of installation apparatus 22, bone 28, and overlying soft tissue 110 (e.g., muscle). Blade 54 may be positioned forward of bone plate 26 and at the same elevation as the bone plate, such that the blade is generally coplanar with the bone plate. At least part of blade 54 may taper in thickness away from the bone plate, that is, generally in the direction of advancement of internal portion 40 and/or inner arm 45. Accordingly, blade 54 may have an outer surface 112 that is at least partially sloped with respect to a plane defined by the internal portion and/or the bone plate. The outer surface may have a sloped area 113 that forms any suitable portion or all of the outer surface. For example, in the present illustration, all of outer surface 112 is sloped. Sloped area 113 may have a linear, concave, and/or convex profile generally along the long axis of internal portion 40. Outer surface 112 may be sloped, on average, at an angle of less than about 25, 20, or 15 degrees, among others. In some embodiments, at least a portion or at least most of outer surface 112 may be at least substantially parallel to a plane defined by the internal portion and/or the bone plate.

Outer surface 112 is separated from an opposing inner surface 114 of the blade by an edge 116. The edge may be sharper than an adjacent leading end of bone plate 26. However, the edge may be dull enough to limit or avoid cutting soft tissue 110, which permits the blade to separate soft tissue 110 from bone 28 by blunt dissection.

Blade 54 may have any suitable length measured parallel to the long axis of the internal portion. For example, the length of the blade may be less than about one-half or less than about one-fourth the length of cavity 92 and/or bone plate 26. In exemplary embodiments, blade 54 may have a length of about 5-25 millimeters or about 10-20 millimeters, among others.

Blade 54 may have any suitable thickness measured perpendicular to a plane defined by the internal portion and/or bone plate. For example, the blade may be thinner than the bone plate, which means that the average thickness of the blade is less than the average thickness of the bone plate. In some embodiments, the entire blade may be thinner than the average thickness of the bone plate or, alternatively, a portion of the blade may be thicker than the average thickness of the bone plate.

Bone plate 26 may be attached to coupling mechanism 90 in an unlocked configuration (e.g., by a friction fit with the internal portion) or in a locked configuration. FIGS. 3 and 4 collectively show an example of how the coupling mechanism may lock the bone plate to the insertion tool. The coupling mechanism may use retention structure disposed on opposing sides of the cavity and/or at opposing ends, among others. The retention structure may include a projection(s) and/or a recess(es) that are complementary to a corresponding recess(es) and/or projection(s) of the bone plate. For example, here, the retention structure includes a detent 132 that is movable (e.g., slidable and/or rotatable) with respect to inner arm 45 of internal portion 40. Movable detent 132 may be received in a generally complementary recess 134 formed in the trailing end of bone plate 26. Movable detent 132 may be biased toward recess 134, such as via a spring 136, or may be held in position by threaded engagement within the bone plate or inner arm 45 of the internal portion, among others. In any event, movable detent 132 may cooperate with opposing retention structure of the bone plate and insertion tool to lock the bone plate to the insertion tool. For example, a fixed detent 138 may be formed at the opposing end of the cavity 92. Fixed detent 138 may be received in a generally complementary recess 140 formed in the leading end of the bone plate or the opposing retention structure may include a recess defined by the internal portion that receives a projection provided by the bone plate.

Coupling mechanism 90 may be adjusted to unlock the bone plate from the insertion tool, for example, after the bone plate is properly positioned on bone and under soft tissue, and, optionally, after the bone plate is secured to bone with fasteners. In particular, the coupling mechanism may be unlocked using an actuator 142 that is coupled to movable detent 132. At least a portion of the actuator may be part of external portion 42, so that the actuator is accessible outside the patient when the internal portion and bone plate are disposed under soft tissue. The actuator thus may be configured to be engaged and operated manually, such as through a knob 143, a lever, a button, and/or the like of the actuator. In the present illustration, knob 143 is connected to movable detent 132 via a rod 144 and may be moved translationally relative to internal portion 40, to release engagement of movable detent 132 with the bone plate by sliding the movable detent. Alternatively, the actuator may be adjusted to unlock the bone plate from the insertion tool by pivotal motion and/or by using a separate instrument to engage and adjust the actuator. In any event, after the movable detent has been moved to unlock the bone plate from the internal portion, the internal portion may be separated from the bone plate by urging the internal portion outward from bone such that the insertion tool is generally above the bone plate. The internal portion then may be retracted over the implant in a reverse direction (opposite to direction 50 of FIG. 2) and moved out through the incision to remove the insertion tool from the patient.

Figure 5:
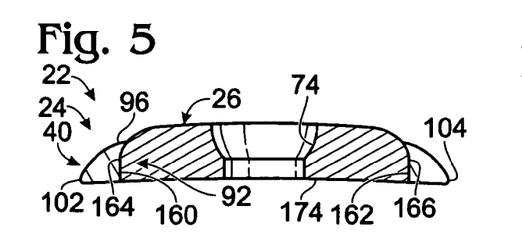
FIG. 5 is a cross-sectional view of the installation apparatus of FIG. 4 in the absence of the humeral bone and overlying soft tissue, taken generally along line 5-5 of FIG. 4.

FIG. 5 shows a cross-sectional view of insertion tool 24 and bone plate 26, taken generally along line 5-5 of FIG. 4. Cavity 92 of internal portion 40 may be narrower towards outer surface 96, to restrict outward movement of the bone plate (i.e., upward in the orientation shown in FIG. 5). For example, spanning members 102, 104 of the internal portion may form opposing lateral walls 160, 162 that are complementary to opposing lateral surfaces 164, 166 of the bone plate, such that cavity 92 tapers toward outer surface 96.

Figure 6:
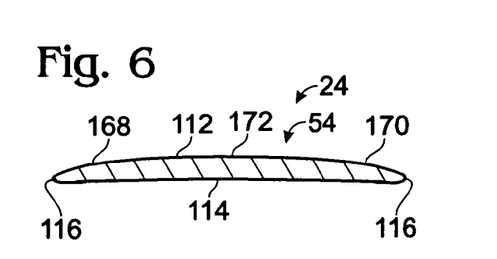
FIG. 6 is a cross-sectional view of a blade of the insertion tool of FIG. 4, taken generally along line 6-6 of FIG. 4.

FIG. 6 shows a cross-sectional view of insertion tool 24 taken generally along line 6-6 of FIG. 4, through blade 54. The blade may taper in opposing lateral directions from a central region of the blade, to form opposing side regions of edge 116. For example, outer surface 112 of blade 54 may include a pair of flanking regions 168, 170 that slope in opposing lateral directions from a central region 172 of blade 54. Alternatively, outer surface 112 may slope laterally in only one direction or may not be sloped laterally. Inner surface 114 of blade 54 may be unsloped (and planar) or may be at least partially sloped longitudinally and/or laterally. For example, as shown here, inner surface 114 may have a transverse curvature that renders the inner surface concave transversely. The transverse curvature of inner surface 114 may correspond to a transverse curvature of an inner surface 174 of the bone plate (see FIG. 5) and/or to a surface region on bone 28. The blade may be flexible enough to permit the transverse curvature of at least a leading portion of the blade to change by transverse flexion, to conform the blade to the shape of the bone surface.

Figure 7:
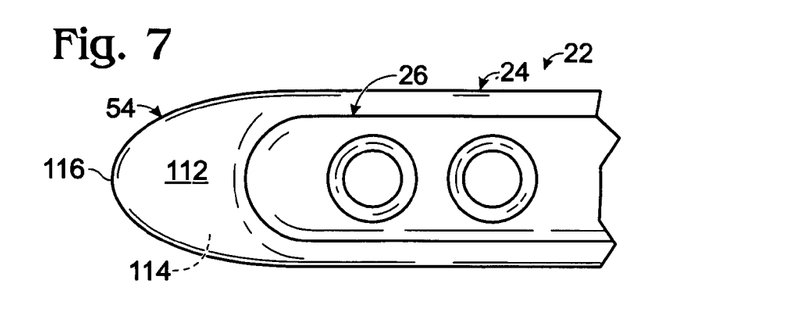
FIG. 7 is a fragmentary plan view of a leading portion of the installation apparatus of FIG. 1.

FIG. 7 shows a fragmentary plan view of a leading portion of installation apparatus 22. Blade 54 may have a rounded perimeter when viewed from generally orthogonal to outer surface 112 and/or inner surface 114 of the blade. Accordingly, edge 116 may be curved.

Figure 8:
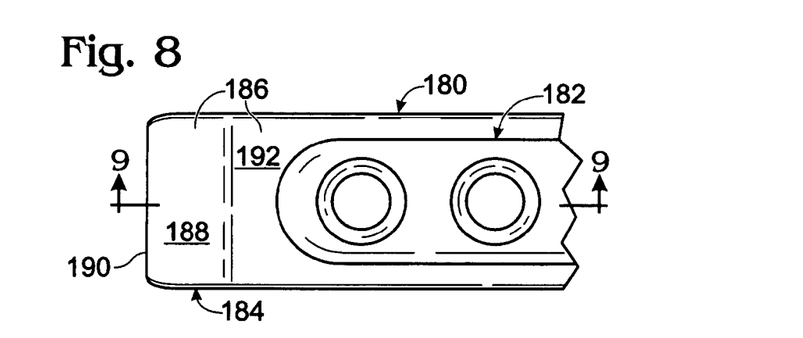
FIG. 8 is a fragmentary plan view of a leading portion of an exemplary installation apparatus having a generally rectangular blade, in accordance with aspects of present disclosure.
Figure 9:
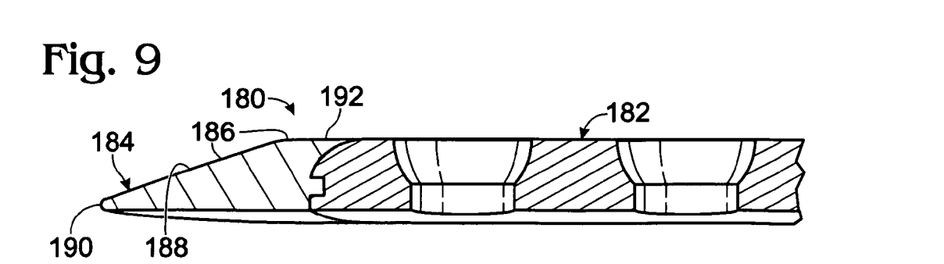
FIG. 9 is a longitudinal sectional view of the installation apparatus of FIG. 8, taken generally along line 9-9 of FIG. 8.

FIGS. 8 and 9 show respective plan and longitudinal sectional views of another exemplary insertion tool 180 coupled to a bone plate 182. Tool 180 may have a generally rectangular blade 184 extending forward of bone plate 182. Blade 184 may have an outer surface 186 including a sloped region 188 that forms a bevel extending generally along a long axis defined by the bone plate and/or the insertion tool to a leading edge 190 of the blade. Blade 184 may be tapered or nontapered laterally. Accordingly, the sloped region 188 may form a planar bevel. Blade 184 also may include a nonsloped region 192 that is at least substantially parallel to a plane defined by the bone plate.

II. Exemplary Methods of Installing a Bone Plate

The present disclosure provides methods of installing a bone plate and of fixing bone using an insertion tool attached to a bone plate. The methods may include any of the steps presented below in this section or elsewhere in the present disclosure. The steps may be performed in any suitable order and in any suitable combination, and each step may be performed any suitable number of times.

A bone may be selected for fixation. Any suitable bone (or bones for a fusion procedure) may be selected. Accordingly, the bone may be a long bone or another bone of the skeleton. The bone selected may be a bone of the arms (such as a humerus, a radius, and/or an ulna), a bone of the legs (such as a femur, a tibia, and/or a fibula), a bone of the hands (such as a carpal, metacarpal, and/or phalange), a bone of the feet (such as a tarsal, metatarsal, and/or phalange), a clavicle, a rib, a scapula, a pelvic bone, a vertebra, a mandible, a cranial bone, and/or the like.

The selected bone may have a discontinuity. The discontinuity may be a pre-existing discontinuity present before surgery and/or a discontinuity introduced during performance of a method of bone fixation. Accordingly, the method may include a step of introducing a discontinuity into the selected bone, such as by cutting or breaking the bone. The bone may have any suitable condition to be treated, including a fracture, a cut, a malunion, a nonunion, a structural weakness, an undesirable length and/or angulation, and/or the like. The condition may affect any suitable portion of the bone, such as a diaphyseal (shaft or central) and/or a metaphyseal (end) region of the bone (e.g., a proximal or distal end region of a long bone). In exemplary embodiments, the selected bone region may be a proximal humerus, a distal radius, or a distal tibia with at least one metaphyseal or shaft fracture or with only one metaphyseal or shaft fracture.

In some embodiments, the method may include creating an incision through soft tissue to access the bone. The step of creating an incision may create one or more incisions at any suitable position(s) relative to the selected bone. For example, an incision may be created longitudinally near an end of a bone (e.g., the proximal end or the distal end of the bone) or more centrally along the bone. In any event, the incision may be substantially shorter than the bone plate to be installed or may be about the same length as or longer than the bone plate. Optionally, and particularly if the incision is substantially shorter than the bone plate, at least a second incision may be created through soft tissue to access the bone plate. The second incision(s) also may be substantially shorter than the length of the bone plate. In addition, the second incision may be disposed more centrally along the bone and/or more toward an end of the bone than the first incision. Each incision (or only one incision) may be created to access any suitable side of the selected bone, such as the anterior, posterior, medial, and/or lateral side of the bone. These and other suitable steps of the methods may be performed under aseptic conditions and/or in an aseptic field, for example, during surgery in an operating room.

An installation apparatus may be selected. Selection of an installation apparatus may include selecting at least one insertion tool and a bone plate that is attached or attachable to the insertion tool. The bone plate thus may be attached to the insertion tool before or after the installation apparatus is selected. The step of selecting an installation apparatus may be based on the bone selected for fixation, for example, based on the type of bone, left/right sidedness of the bone, the target region within the bone for fixation, or any combination thereof, among others. Accordingly, the step of selecting an installation apparatus may include selecting a bone plate and/or an insertion tool sized and/or shaped for use on the bone. For example, the bone plate and/or a blade of the insertion tool may have a nonplanar inner surface that is generally complementary to a nonplanar surface region and/or a surface contour of the bone selected.

Figure 10:
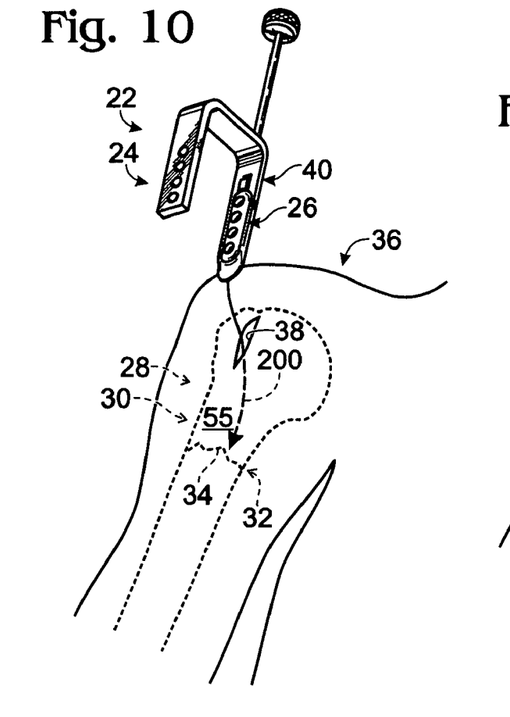
FIG. 10 is a view of the shoulder region of a patient with a fractured proximal humeral bone during performance of an exemplary method of fixing a bone using the installation system of FIG. 1, with a bone plate positioned to be placed on the humeral bone through an incision using an insertion tool, in accordance with aspects of the present disclosure.

FIG. 10 shows a shoulder region of patient 36 on whom an exemplary method of installing a bone plate and fixing a bone is being performed. Proximal humeral bone with fracture 34 has been selected. Installation apparatus 22 also has been selected. A first incision 38 has been created in soft tissue over humeral bone 30 to provide access to the humeral bone.

Installation apparatus may be moved or advanced along a path 200 through first incision 38 and along surface 55 of humeral bone 30 to dispose the bone plate on the bone. Disposing the bone plate on bone may include placing the bone plate and at least part of internal portion 40 of insertion tool 24 through first incision 38. In some embodiments, the bone plate and the insertion tool may be advanced along surface 55 of the bone from the incision such that at least a portion, at least most, or all of the bone plate is nonoverlapping with the incision. Advancement of the bone plate may include moving the bone plate in any suitable direction with respect to bone, such as longitudinally and/or transversely, among others. If the bone plate is moved longitudinally, movement may be toward a central region of the bone and/or toward an end region of the bone, and either proximally or distally along the bone.

Figure 11:
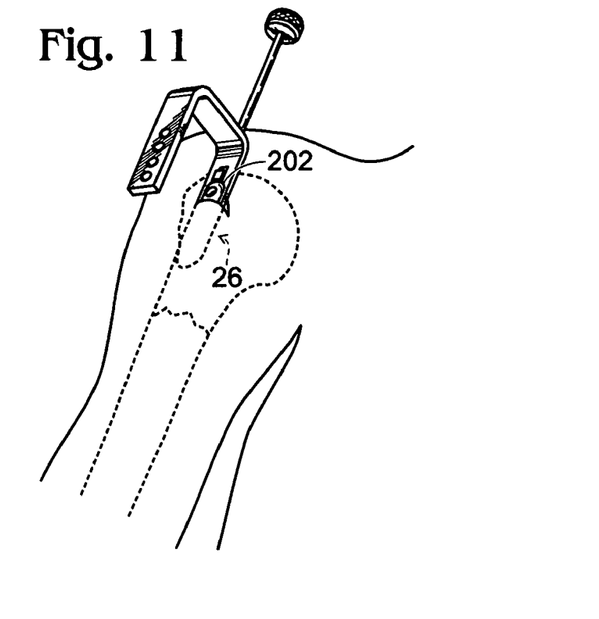
FIG. 11 is a view taken generally as in FIG. 10 during performance of an exemplary method of fixing a bone using the installation system of FIG. 1, with the bone plate partially advanced onto the humeral bone through the incision using the insertion tool, in accordance with aspects of the present disclosure.
Figure 12:
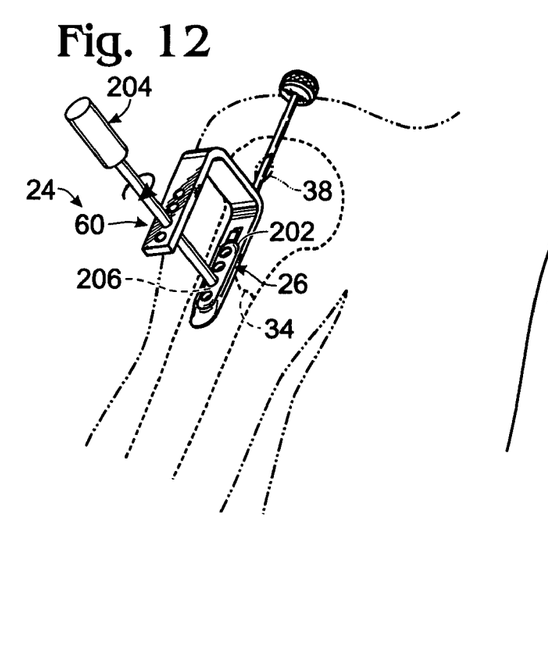
FIG. 12 is a view taken generally as in FIG. 10 during performance of an exemplary method of fixing a bone using the installation system of FIG. 1, with the bone plate fully advanced into position on the humeral bone and being attached to the humeral bone using bone screws, in accordance with aspects of the present disclosure.

FIGS. 11 and 12 show bone plate 26 in respective partially and fully advanced configurations on bone. In FIG. 12, a trailing boundary 202 of the bone plate has been advanced past the border of first incision 38 such that the bone plate does not overlap the first incision. Furthermore, in the fully advanced configuration shown in FIG. 12 bone plate 26 spans fracture 34.

The bone plate may be attached and/or secured to the bone. Attaching/securing the bone plate may be performed with any suitable fasteners, such as one or more threaded fasteners that extend through apertures of the bone and into the bone for threaded engagement with the bone, bone plate, or both. Attaching/securing the bone plate may include forming holes in the bone for receiving fasteners. The holes may be formed by the fasteners themselves, such as by using self-drilling fasteners, or may be formed with a hole-forming tool (i.e., a drill). The path along which each hole is formed and/or fastener is placed in bone may be guided by a wire (a guide wire) extending through an aperture of the bone plate. Alternatively, or in addition, the path may be defined by targeting guide 60 of insertion tool 24. For example, FIG. 12 shows a driver 204 driving a threaded fastener 206 disposed in an aperture of bone plate 26, while guided by targeting guide 60.

The insertion tool may be uncoupled from the bone plate at any suitable time. For example, the insertion tool may be uncoupled before or after the bone is attached to bone and/or fully secured to the bone. The uncoupled insertion tool may be removed from the patient by retracting the insertion tool through the same incision used for advancing the insertion tool into the patient. Alternatively, the insertion tool, and particularly an internal portion of the insertion tool, may be removed by advancing the internal portion through a distinct incision relative to the incision through which the internal portion was introduced (e.g., after uncoupling the internal portion of the insertion tool from an external portion thereof).

Figure 13:
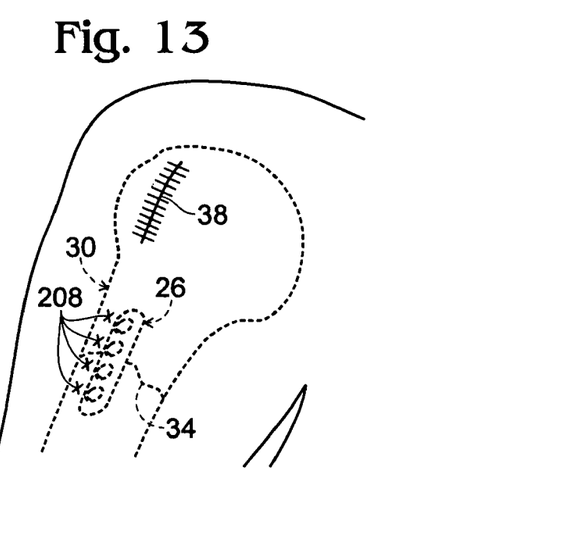
FIG. 13 is a view taken generally as in FIG. 10 during performance of an exemplary method of fixing a bone using the installation system of FIG. 1, with the bone plate attached to the humeral bone and spanning the fracture and after the insertion tool has been uncoupled from the bone plate and removed from the patient's body, in accordance with aspects of the present disclosure.

FIG. 13 shows bone plate 26 installed on and secured to humeral bone 30 with fasteners, and fixing fracture 34. Insertion tool has been removed and primary incision 38 and secondary incisions 208 (formed over each aperture of the bone plate) have been closed with sutures.

III. Composition of System Components

The bone plates, insertion tools, and/or any other system components disclosed herein may be formed of any suitable material(s), including biocompatible material(s) and/or bioresorbable (bioabsorbable) material(s). Exemplary materials that may be suitable for a bone plate and/or an insertion tool include (1) metal (for example, titanium or titanium alloy, cobalt-chrome alloy, stainless steel, etc.); (2) plastic (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) ceramic (for example, alumina, beryllia, calcium phosphate, and/or zirconia, among others); (4) composite (for example, carbon-fiber composites); (5) bioresorbable material (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.); (6) bone material or bone-like material (e.g., bone chips, calcium phosphate crystals (e.g., hydroxyapatite, carbonated apatite, etc.)); and/or (7) any combination thereof, among others.

The bone plate and the insertion tool (or pieces thereof) may be formed of the same or different materials. For example, both the bone plate and the insertion tool may be formed of metal, of the same or different composition, or the bone plate may be formed of metal and at least a portion of the insertion tool (e.g., the blade, the internal portion, the body of the external portion, etc.) may be formed of plastic, among others.

IV. Kits for Installing Bone Plates

The fixation devices of the present disclosure, or any components thereof, may be provided in kits for bone plate installation and/or bone fixation. The kits may include any combination of one or more insertion tools, one or more bone plates that attach to the insertion tools, fasteners for the bone plates, a drill(s), a saw or related cutting tool, instructions for use, or any combination thereof, among others. Some or all of the components of each kit may be provided in a sterile condition, such as packaged in a sterile container.

V. Examples

The following examples describe selected aspects and embodiments of the present disclosure, particularly other exemplary installation apparatus for bone plates. These examples and the various features and aspects thereof are included for illustration and are not intended to define or limit the entire scope of the present disclosure. The various features and aspects of the following examples may be combined with one another or introduced into any of the other insertion tools of the present disclosure in any suitable combination.

Example 1

Insertion Apparatus with Locked Bone Plate

Figure 14:
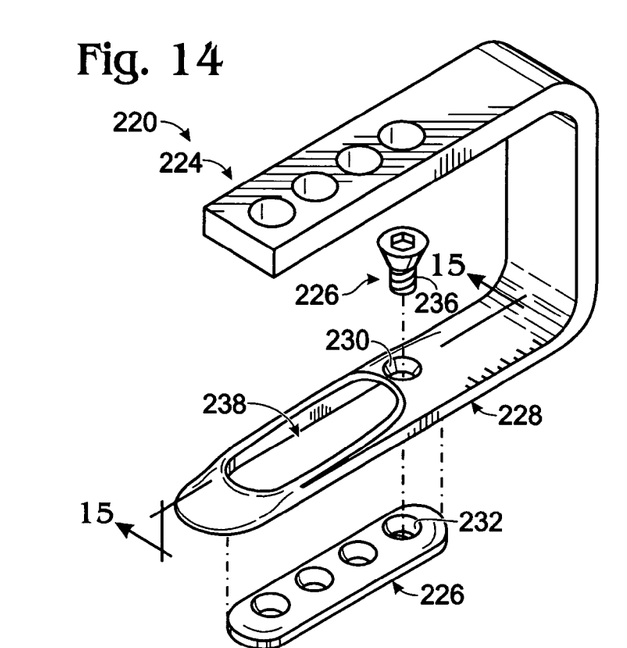
FIG. 14 is an exploded view of another exemplary installation apparatus for bone plates, in accordance with aspects of the present disclosure.
Figure 15:
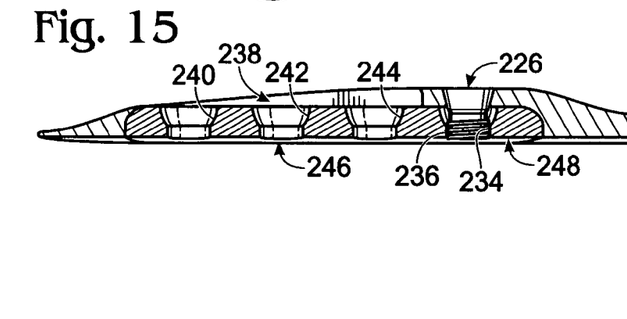
FIG. 15 is a longitudinal sectional view of the installation apparatus of FIG. 14, taken generally along line 15-15 of FIG. 14.

This example describes an exemplary insertion apparatus having a bone plate locked to an insertion tool by threaded engagement with a fastener near an end of the bone plate; see FIGS. 14 and 15.

FIGS. 14 and 15 show respective exploded and sectional views of another exemplary installation apparatus 220 for bone plates. Apparatus 220 includes a bone plate 222 that attaches to an insertion tool 224 via at least one threaded fastener 226. An internal portion 228 of the insertion tool defines an opening 230 that is coaxial with an aperture 232 of the bone plate when the bone plate is received by the internal portion. Aperture 232 may be a locking aperture having an internal thread 234 that engages an external thread 236 of threaded fastener 226, to dispose the threaded fastener in threaded engagement with the bone plate.

Opening 230 may be positioned at any suitable position along internal portion 228 for alignment with any suitable locking aperture of the bone plate. For example, opening 230 may be disposed for alignment with the most rearward aperture of the bone plate, as shown here. Internal portion 228 may define a through-hole 238 forward of opening 230 that permits access to apertures 240-244 defined by a leading portion 246 of the bone plate. In use, the bone plate may be disposed on a bone by advancing the bone plate through a primary incision until only a trailing portion 248 of the bone plate still overlaps the primary incision (and leading portion 246 of the bone plate is covered by soft tissue). With this configuration, threaded fastener 226 is still accessible through the primary incision. Next, the bone plate may be attached/secured to bone, while attached to insertion tool 224, by placing fasteners into apertures 240-244 via through-hole 238 of the insertion tool. The bone plate then may be unlocked from insertion tool 224 by removing threaded fastener 226 and the insertion tool may be retracted. Threaded fastener 226 may be replaced with a bone screw that extends into bone after (or before) the insertion tool has been removed.

Example 2

Insertion Apparatus with Bone Plate Locked Centrally

Figure 16:
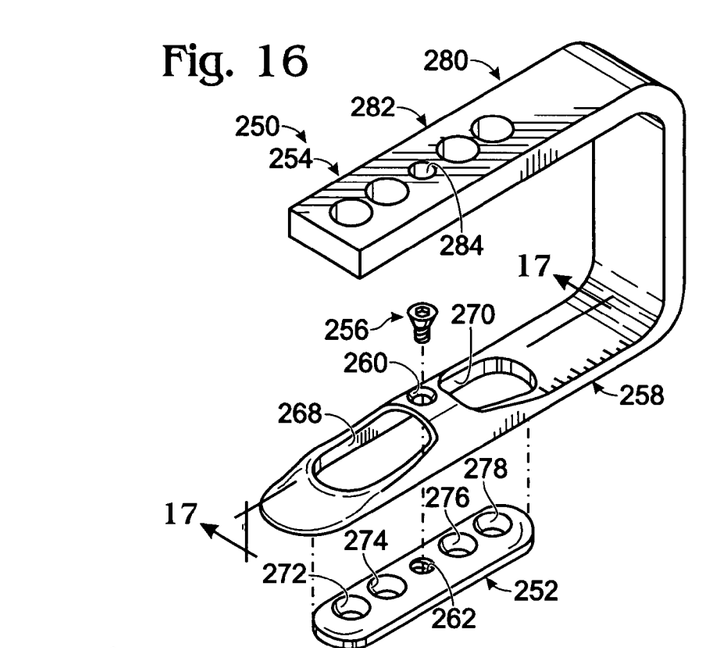
FIG. 16 is an exploded view of yet another exemplary installation apparatus for bone plates, in accordance with aspects of the present disclosure.
Figure 17:
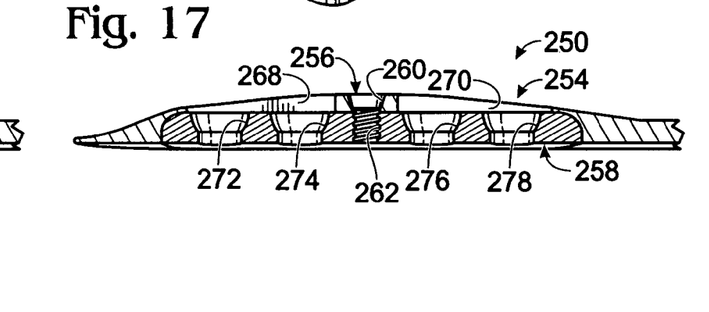
FIG. 17 is a longitudinal sectional view of the installation apparatus of FIG. 16, taken generally along line 17-17 of FIG. 16.

This example describes an exemplary insertion apparatus having a bone plate locked to an insertion tool by threaded engagement with a fastener centrally in the bone plate; see FIGS. 16 and 17.

FIGS. 16 and 17 show respective exploded and sectional views of yet another exemplary installation apparatus 250 for bone plates. Apparatus 250 includes a bone plate 252 that attaches to an insertion tool 254 via at least one threaded fastener 256. An internal portion 258 of the insertion tool defines an opening 260 that is coaxial with an aperture 262 of the bone plate when the bone plate is received by the internal portion. Aperture 262 may be a locking aperture having an internal thread that engages an external thread of threaded fastener 256, to dispose the threaded fastener in threaded engagement with the bone plate.

Opening 260 may be positioned centrally or toward the leading end of bone plate 252. Accordingly, opening 260 may be opposingly flanked by through-holes 268, 270 disposed respectively forward and rearward of opening 260, to provide access to apertures 272-278 of the bone plate. In use, the bone plate may be disposed on a bone by advancing the bone plate through a primary incision until the bone plate no longer overlaps the primary incision. With this configuration, threaded fastener 256 is covered by soft tissue and thus generally is not accessible directly through the primary incision. Next, the bone plate may be attached/secured to bone while attached to insertion tool 254, by placing fasteners into apertures 272-278 via through-holes 268, 270. The bone plate then may be unlocked from insertion tool 254 by accessing and removing threaded fastener 256 through an ancillary incision created over fastener 256 using an external portion 280 of the insertion tool to guide formation of the ancillary incision. In particular, external portion 280 may include a targeting guide 282 defining a guide opening 284 that is coaxial with locking aperture 262. Removal of fastener 256 through the ancillary incision unlocks the insertion tool from the bone plate, which permits retraction of the insertion tool. After removal of tool 254, aperture 262 may be left open or may be replaced with a bone screw, among others.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

The invention claimed is:

1. A method of installing a bone plate, comprising:
   selecting an insertion tool attached to a bone plate, the insertion tool including a holder portion defining an opening in which the bone plate is held substantially coplanar with the holder portion, the holder portion also including a blade formed forward of the bone plate, at least part of the blade being tapered in thickness generally in a direction of advancement defined by the insertion tool; and
   moving the insertion tool in the direction of advancement along a surface of bone such that soft tissue is urged away from the bone by the blade ahead of the bone plate, wherein the bone plate has opposing lateral side surfaces and opposing end surfaces that collectively form a perimeter of the bone plate, and wherein the holder portion at least substantially encircles the perimeter of the bone plate when the holder portion is holding the bone plate.

2. The method of claim 1, wherein the blade is thinner and more flexible than the bone plate.

3. The method of claim 1, wherein the step of selecting selects an insertion tool having a blade that is sharper than an adjacent end of the bone plate.

4. The method of claim 1, wherein the step of selecting selects an insertion tool having a bone plate locked to the insertion tool.

5. The method of claim 1, wherein the bone plate is held with the holder portion at least substantially encircling a perimeter of the bone plate.

6. The method of claim 1, wherein the opening is a through-hole that at least generally corresponds in size to a length and a width of the bone plate.

7. The method of claim 1, wherein the bone plate has opposing end regions, and wherein the holder portion laterally flanks the bone plate from one end region of the bone plate to the other end region of the bone plate.

8. The method of claim 1, further comprising a step of attaching the bone plate to the holder portion before the step of selecting an insertion tool attached to a bone plate.

9. A method of installing a bone plate, the method comprising:
   selecting an insertion tool attached to a bone plate, the insertion tool including a holder portion defining an opening in which the bone plate is held, wherein the holder portion when holding the bone plate has an average height measured orthogonally with respect to an inner surface of the bone plate, and wherein the average height is not substantially greater than an average height of the bone plate;
   moving the insertion tool along a surface of a bone such that soft tissue is urged away from the bone by a blade of the insertion tool disposed ahead of the bone plate;
   advancing the insertion tool to dispose the bone plate under at least a portion of the soft tissue; and
   attaching the bone plate to the bone.

10. The method of claim 9, further comprising a step of attaching the bone plate to the insertion tool.

11. The method of claim 9, further comprising a step of disengaging the insertion tool from the bone plate after the step of attaching the bone plate to the bone.

12. The method of claim 9, where the step of moving is performed with a first portion of the insertion tool disposed inside a patient's body and with a second portion of the insertion tool disposed outside the patient's body and grasped by hand.

13. The method of claim 9, wherein the step of attaching results in attachment of the bone plate to a bone of a patient's body, wherein the bone plate defines a plurality of apertures, wherein the insertion tool includes a targeting guide defining one or more openings that are coaxial with one or more of the apertures, and wherein the targeting guide is disposed outside the patient's body during the step of attaching the bone plate to the bone.

14. The method of claim 9, wherein the insertion tool includes a body that is at least generally U-shaped.

15. The method of claim 9, wherein the blade tapers in thickness away from the bone plate.

16. The method of claim 9, wherein the blade is thinner and more flexible than the bone plate.

17. The method of claim 9, wherein the blade is sharper than an adjacent end of the bone plate and dull enough to permit separation of soft tissue from bone by blunt dissection.

18. The method of claim 9, wherein the bone plate is formed of metal and the blade is formed of plastic.

19. The method of claim 9, wherein the insertion tool includes reference marks configured to permit measurement of an insertion distance of the insertion tool and/or the bone plate under soft tissue.

20. A method of installing a bone plate, comprising:
selecting an insertion tool attached to a bone plate defining a longitudinal axis, the insertion tool including a holder portion defining a through-hole in which the bone plate is held, the through-hole being at least about as long and wide as the bone plate, the holder portion tapering away from the bone plate along the longitudinal axis at a leading end of the holder portion to form a blade;
moving the insertion tool along a surface of bone such that soft tissue is urged away from the bone by the blade; and
attaching the bone plate to the bone.

* * * * *